United States Patent
Jiang et al.

(10) Patent No.: US 12,180,312 B2
(45) Date of Patent: Dec. 31, 2024

(54) COMPOSITION FOR THE IMMEDIATE TERMINATION OF A FREE-RADICAL POLYMERIZATION AND USES THEREOF

(71) Applicant: SPECIALTY OPERATIONS FRANCE, Lyons (FR)

(72) Inventors: Jing Jiang, Shanghai (CN); Ding Wang, Shanghai (CN); David Vanzin, Franklin, TN (US)

(73) Assignee: SPECIALTY OPERATIONS FRANCE, Lyons (FR)

( * ) Notice: Subject to any disclaimer, the term of this patent is extended or adjusted under 35 U.S.C. 154(b) by 242 days.

(21) Appl. No.: 17/775,169

(22) PCT Filed: Nov. 6, 2019

(86) PCT No.: PCT/CN2019/115862
§ 371 (c)(1),
(2) Date: May 6, 2022

(87) PCT Pub. No.: WO2020/038496
PCT Pub. Date: Feb. 27, 2020

(65) Prior Publication Data
US 2022/0411542 A1    Dec. 29, 2022

(51) Int. Cl.
| | | |
|---|---|---|
| *C08F 2/40* | (2006.01) |
| *C07C 45/86* | (2006.01) |
| *C07C 51/50* | (2006.01) |
| *C07C 67/62* | (2006.01) |
| *C07D 279/20* | (2006.01) |

(52) U.S. Cl.
CPC .............. *C08F 2/40* (2013.01); *C07D 279/20* (2013.01)

(58) Field of Classification Search
CPC ......... C08F 2/40; C07D 279/20; C07C 45/86; C07C 51/50; C07C 67/62
See application file for complete search history.

(56) References Cited

U.S. PATENT DOCUMENTS

| | | |
|---|---|---|
| 6,518,374 B1 | 2/2003 | Aichinger et al. |
| 2015/0337056 A1 | 11/2015 | Koch et al. |
| 2018/0171035 A1 | 6/2018 | Marguerre et al. |
| 2019/0177583 A1 | 6/2019 | Prell |
| 2019/0375883 A1 | 12/2019 | Russo et al. |

FOREIGN PATENT DOCUMENTS

| | | |
|---|---|---|
| CN | 109642002 A | 4/2019 |
| CN | 109689720 A | 4/2019 |
| WO | 2017216767 A1 | 12/2017 |
| WO | 2019032990 A1 | 2/2019 |

OTHER PUBLICATIONS

International Search Report issued in corresponding International Application No. PCT/CN2019/115862; mailed Jun. 22, 2020 (4 pages).
Written Opinion of the International Searching Authority issued in corresponding International Application No. PCT/CN2019/115862; dated Jun. 22, 2020 (5 pages).

*Primary Examiner* — Catherine S Branch
(74) *Attorney, Agent, or Firm* — Osha Bergman Watanabe & Burton LLP

(57) ABSTRACT

The invention relates to a composition for the immediate termination of a free-radical polymerization, the use thereof for the stabilization of free-radically polymerizable monomers against free-radical polymerization and a method for the immediate termination of free-radical polymerizations.

17 Claims, No Drawings

COMPOSITION FOR THE IMMEDIATE TERMINATION OF A FREE-RADICAL POLYMERIZATION AND USES THEREOF

TECHNICAL FIELD

The invention relates to a composition for the immediate termination of a free-radical polymerization, the use thereof for the stabilization of free-radically polymerizable monomers against free-radical polymerization and a method for the immediate termination of free-radical polymerizations.

BACKGROUND OF THE INVENTION

Acrylic acid, esters and vinyl monomers are very reactive and prone to polymerize. Unintentional free-radical polymerization can occur, for example, during storage and/or handling of said monomers since both heat and light can initiate free-radical polymerization. In order to avoid unwanted free-radical polymerization said monomers are usually stabilized, in particular by adding of small quantity of polymerization inhibitor, for example para-methoxyphenol (PMP).

Once initiated, unwanted free-radical polymerization is highly exothermic and there exists a risk of fire and/or explosion if this is not controlled. In the event, such runaway polymerization occur, during transport and/or storage, solutions have already been proposed to efficiently and rapidly terminate any unintentional free-radical polymerization of the monomers. The processes to date involve the addition of a known inhibitor solution, notably as described in U.S. Pat. No. 6,518,374 which describes the use of an inhibitor composition containing phenothiazine, at least 50% by weight of N-alkylpyrrolidone and 2.5 to 12.5% by weight of para-methoxyphenol. US 2015/0337056 describes the use of a composition comprising a phenothiazine compound and/or PMP and at least 50% by weight of a solvent wherein the solvent is a terminally etherified derivative of alkylene glycol and/or of polyalkylene glycol. Document US 2018/0171035 discloses a composition capable of stopping unwanted free-radical polymerization and comprising a phenothiazine derivative, an aprotic solvent, and an ionic liquid, the document specifies that said composition display acceptable viscosity, high polymerization inhibitor concentration and is inert toward the monomer. These and other known phenothiazine shortstop solutions are based upon ethyl acetate, isopropyl acetate, acetone and glycol solvents.

However each solution requires the use of solvents which are either toxic, flammable or irritating, in particular alkylpyrrolidones can affect human's health.

It is an object of the present invention to provide a composition capable of immediately terminating unwanted polymerization which displays similar or improved properties, notably in terms of polymerization inhibitor concentration, viscosity or which can be used over a wide range of temperature. In addition, the composition of the present invention is safer and easier to handle, and has a lower impact on the environment.

BRIEF DESCRIPTION OF THE INVENTION

A first object of the present invention relates to a composition comprising:
(i) at least one compound of formula (I):

wherein A is a $C_2$-$C_5$ alkylene, $R_1$, $R_2$ and $R_3$, identical or different, are a $C_1$-$C_6$ alkyl, and
(ii) at least one free-radical polymerization inhibitor.

The present invention also relates to a method for immediately terminating free-radical polymerization by adding a composition according to the present invention to a composition comprising at least one free-radically polymerizable monomer.

Another object of the present invention concerns the use of a composition according to the present invention for stabilizing a free-radically polymerizable monomer and/or for immediately stopping free-radical polymerization of a free-radically polymerizable monomer.

Still another object of the present invention concerns the use of a compound of formula (I) in a composition for stabilizing a free-radically polymerizable monomer and/or for immediately stopping free-radical polymerization of a free-radically polymerizable monomer.

DETAILED DESCRIPTION

In the present disclosure, unless otherwise stated, the expression "comprised between . . . and . . . " includes the limits. In the present disclosure, unless otherwise stated, the expression "comprise" includes the meaning of "consist of".

In the present disclosure, unless otherwise stated, the expression "alkyl" refers to an acyclic, linear or branched alkyl with a general formula of $C_nH_{2n+1}$. A $C_1$-$C_6$ alkyl refers to an alkyl group comprising from 1 to 6 carbon atoms, preferably from 1 to 4 carbon atoms, linear or branched.

Notably the expression "$C_1$-$C_4$ alkyl" refers to a methyl, ethyl, propyl, iso-propyl, n-butyl, s-butyl, tert-butyl.

A first object of the present invention relates to a composition comprising:
(i) at least one compound of formula (I):

wherein A is a $C_2$-$C_5$ alkylene, $R_1$, $R_2$ and $R_3$, identical or different, are a $C_1$-$C_6$ alkyl, and
(ii) at least one free-radical polymerization inhibitor.

Preferably the at least one free-radical polymerization inhibitor is selected from the group consisting of phenothiazine derivative, para-methoxyphenol and TEMPO derivative.

According to the present invention, a compound of formula (I) is an esteramide compound. In a preferred aspect of the present invention, A is a $C_4$ alkylene group, preferably A is an alkylene group of formula —CHMe-CH$_2$—CH$_2$ or of formula —CH$_2$—CH$_2$—CHMe-. In a preferred aspect of the present invention $R_1$, $R_2$ and $R_3$ are $C_1$-$C_4$ alkyls, preferably methyl, ethyl, propyl, iso-propyl, n-butyl, s-butyl, tert-butyl. In a most preferred embodiment, $R_1$, $R_2$ and $R_3$ are methyl groups.

In an aspect of the present invention, the present invention relates to a composition comprising methyl-5-(dimethylamino)-2-methyl-5-oxopentanoate and at least one free-radical polymerization inhibitor, preferably selected from the group consisting of phenothiazine derivative, para-methoxyphenol and TEMPO derivative.

The composition according to the present invention comprises at least one, in particular precisely one, phenothiazine derivative. Phenothiazine derivatives are effective inhibitors for free-radical polymerization. Suitable phenothiazine derivatives are those of general formula (II):

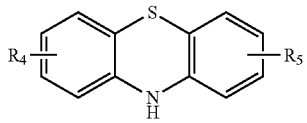

Formula (II)

Wherein $R_4$ and $R_5$ are each, identical or different, selected from the group consisting of H, $C_1$-$C_{12}$-alkyl, preferably $C_1$-$C_6$ alkyl and more preferably $C_1$-$C_4$ alkyl.

Suitable phenothiazine derivatives are phenothiazine, 2-methylphenothiazine, 2-octylphenothiazine, 2-nonylphenothiazine, 2,8-diethylphenothiazine, 3,7-dimetylphenothiazine, 3,7-diethylphenothiazine, 3,7-dibutylphenothiazine, 3,7-dioctylphenothiazine, 2,8-dioctylphenothiazine, 3,7-dinonylphenothiazine, and 2,8-dinonylphenothiazine. Preferably the phenothiazine derivative is phenothiazine ($R_4$=$R_5$=H).

According to another aspect of the present invention, the composition according to the present invention comprises at least one, in particular precisely one, TEMPO derivative.

According to the present invention, the composition comprises two free-radical polymerization inhibitors, preferably one phenothiazine derivative and para-methoxyphenol, or one phenothiazine derivative and a TEMPO derivative.

According to the present invention, the expression "TEMPO derivative" are those of formula (III):

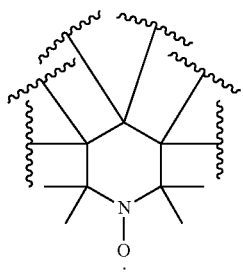

Formula (III)

Preferred TEMPO derivatives are selected from the group consisting of 2,2,6,6-tetramethylpiperazin-1-oxyl (TEMPO), 4-hydroxy-2,2,6,6-tetramethylpiperazin-1-oxyl (OH-TEMPO), and 4-oxo-2,2,6,6-tetramethylpiperazin-1-oxyl (oxo-TEMPO).

According to the present invention, the composition comprises three free-radical polymerization inhibitors.

According to the present invention, the composition can further comprise at least one inhibitor in particular selected from the group consisting of hydroquinone, catechol, 2,6-di-tert-butyl-4-methylphenol (BHT), tert-butylhydroquinone (TBHQ), 4-tert-butylcatechol (TBC), tocopherol derivatives, vitamin E, para-benzoquinone, derivatives of phenylene diamines, aromatic nitro or nitroso derivatives, manganese complexes, preferably manganese acetate, copper complexes having an oxidation state of 2, preferably copper dibutyl dithiocarbamate or copper acetate. According to the present invention, the composition comprises at least 5% by weight of free-radical polymerization inhibitor(s) based on the total weight of the composition, preferably at least 10% by weight, more preferably at least 15% by weight, still more preferably at least 20% by weight and very particularly at least 30% by weight, in particular at least 35% by weight. Generally the composition comprises less than 70% by weight of free-radical polymerization inhibitor(s) based on the total weight of the composition, preferably less than 60% by weight, more preferably less than 50% by weight and still more preferably less than 45% by weight.

According to the present invention, the composition comprises at least 5% by weight of phenothiazine derivative based on the total weight of the composition, preferably at least 10% by weight, more preferably at least 15% by weight, still more preferably at least 20% by weight and very particularly at least 25% by weight, in particular at least 30% by weight. Generally the composition comprises less than 70% by weight of phenothiazine derivative based on the total weight of the composition, preferably less than 60% by weight, more preferably less than 50% by weight and still more preferably less than 45% by weight.

According to an aspect of the present invention, the composition comprises at least 5% by weight of TEMPO derivative based on the total weight of the composition, preferably at least 10% by weight, more preferably at least 15% by weight, still more preferably at least 20% by weight, very particularly at least 25% by weight, still more particularly at least 30% by weight, and most preferably at least 35% by weight. Generally the composition comprises less than 70% by weight of TEMPO derivative based on the total weight of the composition, preferably less than 60% by weight, more preferably less than 50% by weight and still more preferably less than 45% by weight.

Generally the amount of para-methoxyphenol is between 2.5 and 12.5% by weight based on the total weight of the composition.

According to the present invention, the amount of compound of formula (I) is of at least 30% by weight based on the total weight of the composition, preferably at least 40%, more preferably at least 50%, still more preferably at least 60%.

According to the present invention the amount of methyl-5-(dimethylamino)-2-methyl-5-oxopentanoate is of at least 30% by weight based on the total weight of the composition, preferably at least 40%, more preferably at least 50%, still more preferably at least 60%.

According to the present invention, the composition can further comprise a glycol ether solvent, in particular diethylene glycol monomethylether (DEGME), or diethylene glycol monobutylether (DEGBE). Advantageously the use of a glycol ether solvent can improve the solubility of the free-radical polymerization inhibitor(s). Preferably the ratio of compound of formula (I)/glycol ether solvent is of at least 50/50. Generally the ratio of compound of formula (I)/glycol ether solvent is below 80/20. In a preferred aspect, the ratio of methyl-5-(dimethylamino)-2-methyl-5-oxopentanoate/glycol ether solvent is of at least 50/50. Generally the ratio of methyl-5-(dimethylamino)-2-methyl-5-oxopentanoate/glycol ether solvent is below 80/20.

Higher concentrations of the free radical polymerization inhibitor in the composition according to the present invention is advantageous as it allows to reduce inventory and handling of toxic, flammable and irritating solutions and the storage tanks for said composition. Highly concentrated compositions can also improve the incorporation of the inhibitor composition into the free radically polymerizable monomer, especially in the event of uncontrolled/unwanted polymerization.

Additionally, the high boiling point of compounds of formula (I) and in particular of methyl-5-(dimethylamino)-2-methyl-5-oxopentanoate compared to the other solvents allows this composition to be more easily separated from the acrylic acids, esters and monomers and allows for their ready re-use.

Advantageously the composition according to the present invention have a viscosity between 120 and 250 mPa·s at 0° C. (mPa=millipascal). The viscosity may be measured using a Brookfiled viscometer LV. Advantageously the composition according to the present invention have a viscosity between 30 and 100 mPa·s at 10° C. Advantageously the composition according to the present invention have a viscosity between 40 and 65 mPa·s at 20° C. Advantageously the composition according to the present invention have a viscosity between 25 and 35 mPa·s at 30° C. Advantageously, the viscosity is improved or at least equivalent to the viscosity of existing systems (notably comprising phenothiazine in N-methylpyrrolidone). In particular, improved viscosity allows an easy introduction of the composition into the free radically polymerizable monomer, especially by pumping.

Advantageously the composition according to the present invention can be stored at a temperature comprised between −25° C. and 55° C., preferably between −20° C. and 50° C. Advantageously, the composition of the present invention can be stored over a wide range of temperature, no unwanted crystallization or precipitation of the free radical polymerization inhibitor(s) is observed. In particular no crystallization is observer for at least 3 weeks.

The composition according to the present invention is compatible with a wide range of free radically polymerizable monomer. The composition according to the present invention is efficient for immediately stopping unwanted polymerization of free radically polymerizable monomer. In particular the composition according to the present invention is at least as efficient as known systems, in particular phenothiazine alone, or a composition comprising phenothiazine in N-methylpyrrolidone.

According to the present invention, the expression "free radically polymerizable monomer" refers to a monomer which polymerization undergoes a radical process, which can be initiated by light, heat or undesired radicals. According to the present invention, a free-radically polymerizable monomer refers to those substances which comprise at least 95% by weight or at least 98% by weight or at least 99% by weight of vinyl monomers, in particular (meth)acrylic monomers and/or styrene. The term (meth)acrylic monomers is to be understood as meaning of substances which comprise acrolein, methacrolein, acrylic acid, methacrylic acid, acrylic esters and/or methacrylic esters. In particular methyl acrylate, ethyl acrylate, n-butyl acrylate, 2-ethylhexyl acrylate, hydroxyethyl acrylate, hydroxypropyl acrylate, dimethylaminomethyl acrylate, or any other methacrylate derivative, methyl methacrylate, butyl methacrylate, lauryl methacrylate, dimethylaminoethyl methacrylate, and stearyl methacrylate. The term vinyl monomers is to be understood as meaning of substances which comprise a vinyl group —CH=CH$_2$, notably acrylonitrile.

Another object of the present invention relates to a process for the preparation of a composition comprising at least one compound of formula (I) and at least one free-radical polymerization inhibitor, preferably selected from the group consisting of phenothiazine derivative, para-methoxyphenol and TEMPO derivative.

Another object of the present invention relates to a process for the preparation of a composition comprising methyl-5-(dimethylamino)-2-methyl-5-oxopentanoate and at least one free-radical polymerization inhibitor, preferably selected from the group consisting of phenothiazine derivative, para-methoxyphenol and TEMPO derivative.

In particular the at least one free-radical polymerization inhibitor is added to the at least one compound of formula (I), optionally in the presence of a glycol ether solvent. The addition can be performed with or without stirring. Preferably the addition is performed at room temperature, preferably between 15 and 30° C., preferably between 18° C. and 28° C., more preferably between 20° C. and 25° C. The addition is usually performed at atmospheric pressure. The addition may be performed under air, or under inert atmosphere.

Another object of the present invention relates to the use of a composition according to the present invention for stabilizing a composition comprising at least one free-radically polymerizable monomer or for immediately stopping free-radical polymerization of a composition comprising at least one free-radically polymerizable monomer.

In another aspect, the present invention relates to a method for immediately terminating free-radical polymerization by adding a composition according to the present invention to the free-radical polymerization system.

The beginning of the unwanted polymerization may be recorded by detection of a heat increase in the free radical polymerization system. The unwanted polymerization may occur in a reactor or during storage, transport or handling of the free radical polymerization system.

Advantageously, the composition according to the present invention can be added to a composition comprising at least one free-radically polymerizable monomer via a spray nozzle, in order to achieve the most rapid homogeneous distribution. The composition may also be added by pumping and/or stirring.

Finally, the present invention relates to the use of a compound of formula (I) in a composition for stabilizing a free-radically polymerizable monomer and/or for immediately stopping free-radical polymerization of a free-radically polymerizable monomer.

EXAMPLES

Example 1 (Comparative): Composition comprising 35% phenothiazine, 5% para-methoxyphenol in 60% by weight of N-methyl-2-pyrrolidone according to U.S. Pat. No. 6,518,374.

Example 2 (Invention): Composition comprising 30% phenothiazine, 5% para-methoxyphenol in 65% by weight of RhodiaSolv® Polarclean (comprising methyl-5-(dimethylamino)-2-methyl-5-oxopentanoate).

Example 3 (Invention): Composition comprising 30% phenothiazine in 70% by weight of RhodiaSolv® Polarclean (comprising methyl-5-(dimethylamino)-2-methyl-5-oxopentanoate).

Example 4 (Invention): Composition comprising 30% by weight of phenothiazine, in RhodiaSolv® Polarclean/diethylene glycol monomethylether (80/20).
Results:

|  | Example 1 | Example 2 | Example 3 | Example 4 |
|---|---|---|---|---|
| Compatibility test | No precipitation | No precipitation | No precipitation | No precipitation |
| Storage stability at −20° C. | No precipitation | No precipitation | No precipitation | No precipitation |

|  | Example 1 | Example 2 | Example 3 | Example 4 |
|---|---|---|---|---|
| Storage stability at 5° C. | No precipitation | No precipitation | No precipitation | No precipitation |
| Storage stability at 20° C. | No precipitation | No precipitation | No precipitation | No precipitation |
| Storage stability at 50° C. | No precipitation | No precipitation | No precipitation | No precipitation |
| Application test | No gelling | No gelling | No gelling | No gelling |
| Viscosity (mPa · s) at 0° C. | 229 | 188 | 58 | 51 |

Compatibility test: Dissolve composition in acrylic acid at 1000 ppm of phenothiazine. Visual inspection of precipitation or layering.

Storage stability: Keep the composition at −20° C., 5° C., 20° C. or 50° C. for 3 weeks. Visual inspection of precipitation.

Application test: Dissolve composition at 50 ppm phenothiazine loading into acrylic acid. Heat for 72 hours at 100° C. Visual inspection of gelling or viscosity increase in the monomer.

Viscosity: The viscosity is measured using a Brookfield viscometer LV at 0° C. and the viscosity test procedure is listed below:
1. Put approx. 35 ml samples into 40 ml glass bottle.
2. Keep the glass bottle in the mixture of ice and water for 30 minutes to make sure the temperature of sample get 0° C.
3. Turn on the viscometer switch, select spindle type S63 and install, then set speed at 100 rpm.
4. Put the glass bottle under spindle to make sure solution level of the glass bottle immersing the tick mark of spindle.
5. Start testing and record reading on the panel.

The results of Example 2-4 demonstrate that the composition of the present invention are at least equivalent to the composition of Example 1, while displaying lower viscosity and improved environmental and health benefits.

The invention claimed is:

1. A composition comprising:
(i) at least one compound of formula (I):

wherein A is a $C_2$-$C_5$ alkylene, $R_1$, $R_2$ and $R_3$, identical or different, are a $C_1$-$C_6$ alkyl, and
(ii) at least one free-radical polymerization inhibitor.

2. The composition according to claim 1 wherein the at least one free-radical polymerization inhibitor is selected from the group consisting of phenothiazine derivative, para-methoxyphenol and TEMPO derivative.

3. The composition according to claim 1 wherein the at least one compound of formula (I) is methyl-5-(dimethylamino)-2-methyl-5-oxopentanoate.

4. The composition according to claim 1 wherein the amount of the at least one compound of formula (I) is of at least 30% by weight based on the total weight of the composition.

5. The composition according to claim 2 wherein the phenothiazine derivative is a compound of general formula (II):

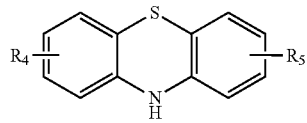

wherein $R_4$ and $R_5$ are each, identical or different, selected from the group consisting of H, and $C_1$-$C_{12}$-alkyl.

6. The composition according to claim 1 comprising at least 5% by weight of the at least one free-radical polymerization inhibitor based on the total weight of the composition.

7. The composition according to claim 2 comprising between 2.5 and 12.5% by weight of the para-methoxyphenol based on the total weight of the composition.

8. The composition according to claim 1 further comprising a glycol ether solvent.

9. The composition according to claim 1 comprising at least one further inhibitor selected from the group consisting of hydroquinone, catechol, 2,6-di-tert-butyl-4-methylphenol (BHT), tert-butylhydroquinone (TBHQ), 4-tert-butylcatechol (TBC), tocopherol derivatives, vitamin E, para-benzoquinone, derivatives of phenylene diamines, aromatic nitro or nitroso derivatives, manganese complexes, and copper complexes having an oxidation state of 2.

10. A method for immediately terminating free-radical polymerization, comprising: adding the composition according to claim 1 to a composition comprising at least one free-radically polymerizable monomer.

11. The method according to claim 10 wherein the free-radically polymerizable monomer comprises acrylonitrile, acrolein, methacrolein, acrylic acid, methacrylic acid, acrylic esters and/or methacrylic esters.

12. A method of stabilizing a free-radically polymerizable monomer, comprising: adding the composition of claim 1 to a composition comprising at least one free-radically polymerizable monomer.

13. The method according to claim 12, wherein the free-radically polymerizable monomer comprises acrylonitrile, acrolein, methacrolein, acrylic acid, methacrylic acid, acrylic esters, and/or methacrylic esters.

14. The composition according to claim 4 wherein the amount of the at least one compound of formula (I) is of at least 50% by weight based on the total weight of the composition.

15. The composition according to claim 6 comprising the at least one free-radical polymerization inhibitor is present at at least 20% by weight of based on the total weight of the composition.

16. The composition according to claim 8 wherein the glycol ether solvent is diethylene glycol monomethylether (DEGME), or diethylene glycol monobutylether (DEGBE).

17. The composition according to claim 9, wherein the at least one further inhibitor is manganese acetate, copper dibutyl dithiocarbamate or copper acetate.

* * * * *